United States Patent
Nakajima

(10) Patent No.: US 9,131,997 B2
(45) Date of Patent: Sep. 15, 2015

(54) HOODED SIMPLE SUCTION TRAY FOR DENTAL EXTRAORAL OPERATIONS

(71) Applicant: Yuko Nakajima, Kitakyushu (JP)

(72) Inventor: Yuko Nakajima, Kitakyushu (JP)

( * ) Notice: Subject to any disclaimer, the term of this patent is extended or adjusted under 35 U.S.C. 154(b) by 0 days.

(21) Appl. No.: 14/390,698

(22) PCT Filed: Nov. 7, 2013

(86) PCT No.: PCT/JP2013/080962
§ 371 (c)(1),
(2) Date: Oct. 3, 2014

(87) PCT Pub. No.: WO2014/077378
PCT Pub. Date: May 22, 2014

(65) Prior Publication Data
US 2015/0072305 A1  Mar. 12, 2015

(30) Foreign Application Priority Data

Nov. 16, 2012  (JP) .................................. 2012-252382

(51) Int. Cl.
| | | |
|---|---|---|
| *B24B 55/06* | (2006.01) | |
| *B24B 55/12* | (2006.01) | |
| *A61C 19/00* | (2006.01) | |
| *A61C 17/06* | (2006.01) | |
| *A61C 13/00* | (2006.01) | |

(52) U.S. Cl.
CPC ............ *A61C 19/007* (2013.01); *A61C 13/0024* (2013.01); *A61C 17/04* (2013.01)

(58) Field of Classification Search
CPC .. A61C 19/007; A61C 13/0023; A61C 55/06; A61C 55/04; A61C 55/12; A61C 55/102; A61C 55/052

USPC .................................. 451/456, 455, 453, 451
See application file for complete search history.

(56) References Cited

U.S. PATENT DOCUMENTS

| | | | | | |
|---|---|---|---|---|---|
| 1,742,331 | A | * | 1/1930 | Voigt ............................. | 451/453 |
| 3,510,945 | A | * | 5/1970 | Linn et al. ....................... | 433/79 |
| 4,824,083 | A | * | 4/1989 | Cattani ........................... | 269/15 |
| 4,952,146 | A | * | 8/1990 | Doty ............................... | 433/77 |
| 5,529,533 | A | * | 6/1996 | Kantrowitz et al. .......... | 451/456 |
| 6,159,086 | A | * | 12/2000 | McClurkin .................... | 451/453 |
| 8,246,420 | B1 | * | 8/2012 | Galati ............................ | 451/89 |
| 2003/0073395 | A1 | * | 4/2003 | Faccin et al. ................. | 451/456 |

FOREIGN PATENT DOCUMENTS

| | | |
|---|---|---|
| EP | 1709941 A1 | 10/2006 |
| JP | S57-057819 U | 4/1982 |

(Continued)

*Primary Examiner* — Robert Rose

(57) ABSTRACT

An object of the invention is to provide a hooded simple suction tray for dental extraoral operations which can be hooked to an upper surface of a table and which enables not only suction of solids and foul-smelling gases resulting from operations but also suction of used liquids during extraoral operations using liquids. The hooded simple suction tray includes: a tray main body with a bottom plate partly serving as a base hooking and mounting portion with a flat lower surface; a communication pipe attached to a portion of the bottom plate other than the base hooking and mounting portion and allowing the tray main body to communicate with a suction hose of a dental suction apparatus; and a fly prevention hood erected at an upper edge of a peripheral side plate of the tray main body to prevent flying substances resulting from an extraoral operation from flying around.

1 Claim, 6 Drawing Sheets

(56) References Cited

FOREIGN PATENT DOCUMENTS

| JP | S59-119811 U | 8/1984 |
|---|---|---|
| JP | H09-224958 A | 9/1997 |
| JP | 2001-037783 A | 2/2001 |
| JP | 2007-130137 A | 5/2007 |
| JP | 2008-289650 A | 12/2008 |
| JP | 2012-095698 A | 5/2012 |

* cited by examiner

HOODED SIMPLE SUCTION TRAY FOR DENTAL EXTRAORAL OPERATIONS

CROSS REFERENCE TO RELATED APPLICATION

This application claims priority based on 35 U.S.C. 119 from prior Japanese Patent Application No. 2012-252382 filed on Nov. 16, 2012, the entire contents of which are incorporated herein by reference.

BACKGROUND OF THE INVENTION

1. Field of the Invention

The present invention relates to a hooded simple suction tray for dental extraoral operations, and more specifically to a suction hood for denture adjustment operations which, when a grinding operation such as denture adjustment or a washing operation for a denture is extraorally performed, allows the operation to be smoothly performed without causing grinding chips or washing water to fly around.

2. Description of Related Art

In a dental treatment room, a grinding operation such as denture adjustment is extraorally performed, and extraoral operations such as washing of a ground denture are performed using a medical tray as a saucer. In that regard, denture grinding chips and powder flying around during grinding and droplets of washing water splashed on the denture during washing may float in the dental treatment room or fall on the floor of the room. This may cause various oral indigenous microorganisms propagating in human oral cavities to grow proliferously in the dental treatment room. As a result, dental treatment may lead to secondary infection caused by the oral indigenous microorganisms.

As a conventional technique for solving this problem, for example, a "universal pipe arm apparatus for a dental treatment flying substance suction apparatus" in Patent Literature 1 is known. This conventional apparatus includes a universal arm that enables free movement of a suction port of the dental treatment flying substance suction apparatus and a base on which a suction pipe is erected so as to face upward generally in the vertical direction; a lower end of a universal arm attachment pipe providing one end side of the universal arm can be removably fitted into the suction pipe.

Thus, during extraoral denture adjustment using this apparatus, a dentist manually operates and moves the universal arm to place the suction port above a table for denture adjustment near a dental unit. Subsequently, the dental treatment flying substance suction apparatus is actuated to perform denture adjustment using a hand piece or the like. As a result, grinding chips and powder flying around during denture adjustment can be sucked into the dental treatment flying substance suction apparatus from the suction port through the universal arm.

PATENT LITERATURE

Patent Literature 1: Japanese Patent Application Laid-open No. 2008-289650

However, since indispensable constituent features according to Patent Literature 1 are the universal arm that moves the suction port and the base on which the suction pipe with the lower end of the universal arm attachment pipe removably installed therein is erected, the whole suction apparatus including the universal pipe arm apparatus is large in size and very expensive.

Moreover, the "universal pipe arm apparatus for the dental treatment flying substance suction apparatus" in Patent Literature 1 includes no suction function for used washing water resulting from washing of the denture and thus needs a saucer such as a medical tray in which the used washing water is collected as in the case of the other conventional techniques.

SUMMARY OF THE INVENTION

An object of the present invention is to provide a hooded simple suction tray for dental extraoral operations which can be hooked to an upper surface of a table and which enables a reduction in the overall size and costs of the suction apparatus, the hooded simple suction tray allowing execution of a process of not only sucking solids and foul-smelling gases resulting from dental operations but also sucking used liquids during extraoral operations using various liquids.

An aspect of the invention set forth in Claim 1 is a hooded simple suction tray for dental extraoral operations which is installed in a suction hose for a dental suction apparatus incorporated in a dental unit and which is removably held by a nozzle holder of the dental unit, wherein the hooded simple suction tray includes: a tray main body having an internal space in which an extraoral operation is performed; a communication pipe that allows the internal space of the tray main body and the suction hose to communicate with each other; and a fly prevention hood that prevents a flying substance resulting from the extraoral operation from flying around, the tray main body, the communication pipe, and the fly prevention hood being integrally formed of a synthetic resin, and wherein the tray main body includes a substantially rectangular bottom plate that is long in an X1-X2 direction and short in a Y1-Y2 direction orthogonal to the X1-X2 direction in a plan view and a peripheral side plate that stands from a peripheral portion of the bottom plate and inclining gradually outward in an upward direction, the bottom plate includes a base hooking and mounting portion formed on the bottom plate and having a partly flat lower surface, the communication pipe extends downward from the bottom plate and is attached to an X2-side end portion of the bottom plate in the X1-X2 direction, with this X2-side end portion being corresponding to an intermediate portion of the bottom plate in the Y1-Y2 direction, the communication pipe is a funnel-shaped pipe that has a diameter gradually increasing upward, the fly prevention hood includes a petal-like plate which is erected at a communication pipe-side upper end portion of the peripheral side plate and which gradually decreases outward in length in the Y1-Y2 direction, gently recessed finger placing portions are arranged in an area of the base engaging and placing portion, on junctions of an upper edge of the peripheral side plate which are connected to opposite ends of the fly prevention hood in the Y1-Y2 direction, the bottom plate has a maximum length of 6 cm to 8 cm in the X1-X2 direction and a maximum length of 2 cm to 6 cm in the Y1-Y2 direction, and the base hooking and mounting portion is hooked to and mounted at an end portion of an upper surface of a work table to allow the extraoral operation to be performed.

According to the invention set forth in Claim 1, the hooded simple suction tray is connected to the suction hose extending from the dental suction apparatus via the communication pipe. For example, during an operation for denture adjustment, the base hooking and mounting portion with the flat lower surface is hooked to the end of the working table, and the hooded simple suction tray is attached to the working table. Thus, during the use of the hooded simple suction tray, the orientation of the tray is stabilized. Subsequently, in the internal space of the tray main body, adjustment operations for the denture such as cutting, grinding, and polishing are performed, and for example, the denture is washed using washing water. While prevented by the fly prevention hood from flowing out from the tray, flying substances such as denture chips and powder and used washing water which result from the operations are sucked into the dental suction apparatus through the suction hose and the communication pipe under a negative pressure generated by the dental suction apparatus. Substances having failed to be sucked, for example, large denture chips, are collected on the bottom plate of the hooded simple suction tray.

Thus, compared to the conventional suction apparatus, the suction apparatus according to the present invention can be reduced in overall size and costs and can suck not only solids such as denture chips and powder resulting from extraoral operations and foul smell and gas resulting from the operations but also liquids such as washing water used during the operations, without using a conventional medical tray or the like and without causing the solids, small, gas, and liquids to fly around.

In particular, during extraoral operations, the operator can perform the operation with the operator's fingers placed (hooked) on the finger placing portions at the junctions of the upper edge of the peripheral side plate which are connected to the opposite ends of the fly prevention hood in a width direction thereof. Thus, the operator's hands are unlikely to be fatigued even if the extraoral operation takes much time.

The "dental extraoral operations" as used herein may be, for example, a denture adjustment operation, a prosthesis polishing operation, and a washing operation. The operator performing a "dental extraoral operation" refers to, for example, a dentist, a dental hygienist, or a dental technician.

The "flying substances" as used herein refer to, for example, denture chips, denture powder, and used washing water resulting from denture adjustment operations.

Furthermore, the "hooded simple suction tray for dental extraoral operations" is a tray (cover) with a fly prevention hood connected to the suction hose extending from the dental suction apparatus and used during a dental extraoral operation by being hooked to a working table, the hooded simple suction tray collecting and guiding flying substances resulting from the operation to the suction hose, under a negative pressure exerted by the dental suction apparatus.

The tray main body includes the bottom plate and the peripheral plate standing from the outer peripheral edge of the bottom plate. A material for the tray main body may be, for example, various types of plastic or various types of metal. To make contamination visible and enhance high-class appearance and cleanliness of the tray, the tray main body may be transparent or translucent. This allows the tray to be easily sterilized and disinfected. The tray main body may have any shape, for example, the tray main body may appear to be rectangular, circular, or ellipsoidal in plan view.

The tray main body is sized so as to be held in one hand.

The "base hooking and mounting portion" is a portion of the tray main body which is utilized when the hooded simple suction tray is mounted by being hooked to the end portion of the upper surface of the working table. The lower surface (back surface) of the bottom plate of the base hooking and mounting portion is flat (flat surface) so that the hooded simple suction tray is stably mounted when the base hooking and mounting portion is hooked to the working table. An upper surface of the base hooking and mounting portion may be a flat surface or a curved surface.

The dental suction apparatus is a negative-pressure generation apparatus (vacuum apparatus) used for dental care.

The suction hose as used herein may be dedicated to the hooded simple suction tray or may be a common suction hose for the oral cavity which sucks saliva and flying substances produced in the oral cavity during dental treatment.

A material for the communication pipe may be, for example, similar to the material for the tray main body. To allow contamination to be easily noticed, the communication pipe may also be transparent or translucent. The communication pipe is molded integrally with the tray main body. The communication pipe may be shaped like a funnel with a diameter gradually increasing upward (the direction in which the communication pipe communicates with the bottom plate). The communication pipe may be formed to have a diameter decreasing in stages toward a tip of the communication pipe so as to be fitted in a suction hose with a different inner diameter.

The fly prevention hood is a plate material standing from a part of the upper edge of the peripheral side plate of the tray main body. A material for the communication pipe may be, for example, similar to the material for the tray main body and the communication pipe. To allow contamination to be easily noticed, the fly prevention hood may be transparent or translucent. The fly prevention hood is molded integrally with the tray main body. The fly prevention hood may shaped like, for example, a flat plate or may appear like a gutter (shaped like, for example, a circular arc, the character U, or the character C) with an opening side thereof facing the inside of the tray main body The "finger placing portion" as used herein is a portion of the hooded simple suction tray on which the operator hooks the operator's finger to rest the operator's hand during a dental extraoral operation.

The expression "gently recessed at the junctions of the upper edge of the peripheral side plate which are connected to the opposite ends of the fly prevention hood in the width direction thereof" means that the finger placing portions are curved in a recess form so as to continue smoothly with the junctions (in circular arc form or the like) between the line of the upper edge of the peripheral side plate and the lines of the opposite ends of the fly prevention hood in the width direction thereof, rather than being curved at a predetermined angle (an acute angle, a right angle, or an obtuse angle).

With respect to the size and shape of the "finger placing portion", the finger placing portion is shaped like a gentle recess with a size enough to allow a male adult to hook the adult's finger on the finger placing portion. The finger placing portion may be provided with, for example, an inner flange portion or an outer flange portion (with a width of 0.5 cm to 3 cm) at an upper edge of the finger placing portion in order to further stabilize a state where the finger is placed on the finger placing portion.

Advantageous Effects of the Invention

According to the invention set forth in Claim 1, the hooded simple suction tray is connected to the suction hose extending from the dental suction apparatus via the communication pipe. For example, during an operation for denture adjustment, the base hooking and mounting portion with the flat lower surface is hooked to the end of the working table, and the hooded simple suction tray is attached to the working table. Thus, during the use of the hooded simple suction tray, the orientation of the tray is stabilized. Subsequently, in the internal space of the tray main body, adjustment operations for the denture such as cutting, grinding, and polishing are performed, and for example, the denture is washed using washing water. While prevented by the fly prevention hood from flowing out from the tray, flying substances such as denture chips and powder and used washing water which result from the operations are sucked into the dental suction apparatus through the suction hose and the communication pipe under a negative pressure generated by the dental suction apparatus. Substances having failed to be sucked, for example, large denture chips, are collected on the bottom plate of the hooded simple suction tray.

Thus, compared to the conventional suction apparatus, the suction apparatus according to the present invention can be reduced in overall size and costs and can suck not only solids such as denture chips and powder resulting from extraoral operations and foul smell and gas resulting from the operations but also liquids such as washing water used during the operations, without using a conventional medical tray or the like and without causing the solids, small, gas, and liquids to fly around.

In particular, during extraoral operations, the operator can perform the operation with the operator's fingers placed on the finger placing portions at the junctions of the upper edge of the peripheral side plate which are connected to the opposite ends of the fly prevention hood in a width direction thereof. Thus, the operator's hands are unlikely to be fatigued even if the extraoral operation takes much time.

DESCRIPTION OF EMBODIMENTS

Figure 1:
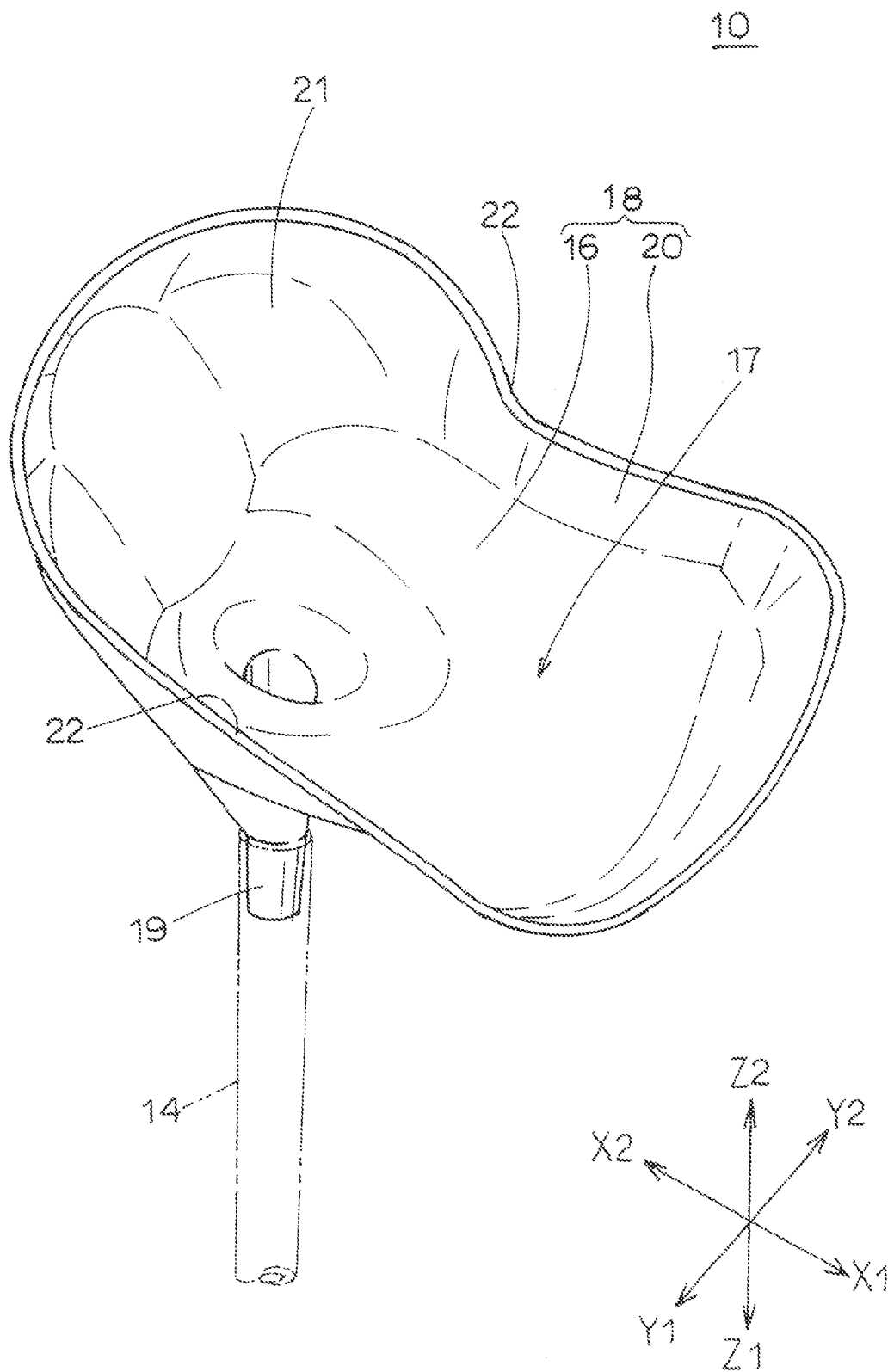
FIG. 1 is a perspective view of a hooded simple suction tray for dental extraoral operations according to Embodiment 1 of the present invention.

An embodiment of the present invention will be specifically described below. For convenience of description, the following definition is used herein. An X1 direction refers to a forward direction of a hooded simple suction tray. An X2 direction refers to a rearward direction of the hooded simple suction tray. A Y1 direction refers to a leftward direction of the hooded simple suction tray. A Y2 direction refers to a rightward direction of the hooded simple suction tray. A Z1 direction refers to an upward direction of the hooded simple suction tray.
Embodiment In FIG. 1 and FIG. 2, reference numeral 10 denotes a hooded simple suction tray for dental extraoral operations (hereinafter simply referred to as a simple suction tray) according to Embodiment 1 of the present invention. The simple suction tray 10 is installed in a suction hose 14 of a dental suction apparatus 13 incorporated in a dental unit 11. The simple suction tray 10 is removably held by a nozzle holder 15.

Figure 4:
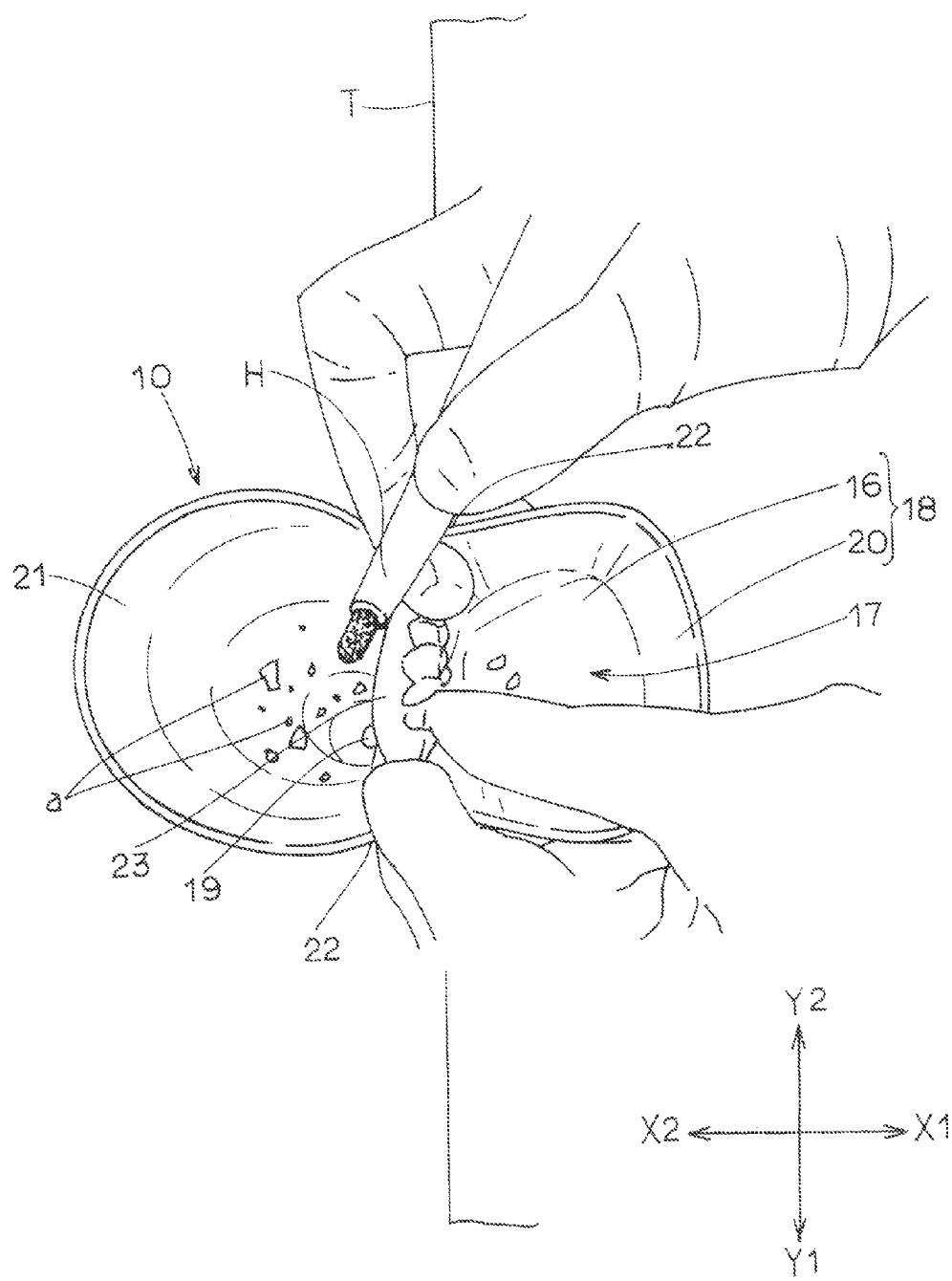
FIG. 4 is a plan view depicting a denture grinding operation state using the hooded simple suction tray for dental extraoral operations according to Embodiment 1 of the present invention.

The simple suction tray 10 includes a tray main body 18 with a bottom plate 16 partly serving as a base hooking and mounting portion 17 with a flat bottom surface, a communication pipe 19 attached to a portion of the bottom plate 16 other than the base hooking and mounting portion 17 in communication with an internal space of the tray main body 18, the communication pipe 19 allowing the tray main body 18 to communicate with the suction hose 14 of the dental suction apparatus 13, and a fly prevention hood 21 erected at an upper edge of a peripheral side plate 20 of the tray main body 18 to prevent flying substances (a) resulting from an extraoral operation including denture adjustment from flying around (FIG. 4). These components are all integrally formed of a synthetic resin.

The components are specifically described below with reference to FIG. 1 and FIG. 3.

The tray main body 18 is a dish-like container (saucer) including the rectangular bottom plate 16 that is long in the X1-X2 direction in plan view and the peripheral side plate 20 standing from a peripheral portion of the bottom plate 16. However, the bottom plate 16 is gently deformed such that the width of an intermediate portion of the bottom plate 16 in the X1-X2 direction is shorter than a normal portion. Furthermore, the peripheral side plate 20 is inclined gradually outward all over the periphery of the peripheral side plate 20 as the peripheral side plate 20 extends upward (FIG. 3).

The bottom plate 16 is 6 cm to 8 cm in length (maximum length in the X1-X2 direction) and 2 cm to 6 cm in width (maximum length in the Y1-Y2 direction). A constricted portion (thin portion) of the bottom plate 16 is 1.5 cm to 5 cm in width.

An upper end of the communication pipe 19 is attached to an X2-side end of the bottom plate 16 at an intermediate portion of the bottom plate 16 in the Y1-Y2 direction in communication with the internal space of the tray main body 18. The peripheral side plate 20 is 0.5 cm to 6 cm in height. Thus, the tray main body 18 and the simple suction tray 10 are each approximately equal to the palm in size.

The communication pipe 19 is a funnel (trumpet)-shaped pipe with a diameter gradually increasing upward. The communication pipe 19 is inserted into a tip portion of the suction hose 14 formed of the synthetic resin.

The fly prevention hood 21 is a petal-shaped plate erected at an X2-side upper edge of the peripheral side plate 20 and having a width gradually decreasing in the X2 direction.

Furthermore, a gently recessed finger placing portion 22 is arranged (formed) at junctions of the upper edge of the peripheral side plate 20 which are connected to the opposite ends of the fly prevention hood 21 in a width direction of the fly prevention hood 21; the finger placing portion 22 is formed in a size that allows a male adult's finger to be placed on the finger placing portion 22. As depicted in FIG. 3, the portions of upper edge of the peripheral side plate 20 on which the finger placing portion 22 is disposed preferably correspond to the area of the base hooking and mounting portion 17 of the bottom plate 16. Thus, during an operation, with a finger being placed, a force exerted on the finger placing portions 22 is received directly by a working table T immediately below the tray via the base hooking and mounting portion 17. Thus, the fly prevention hood 21 is unlikely to slip off from the working table T during the operation.

Now, a method for extraoral denture adjustment using the hooded simple suction tray 10 according to Embodiment 1 of the present invention will be described.

Figure 2:
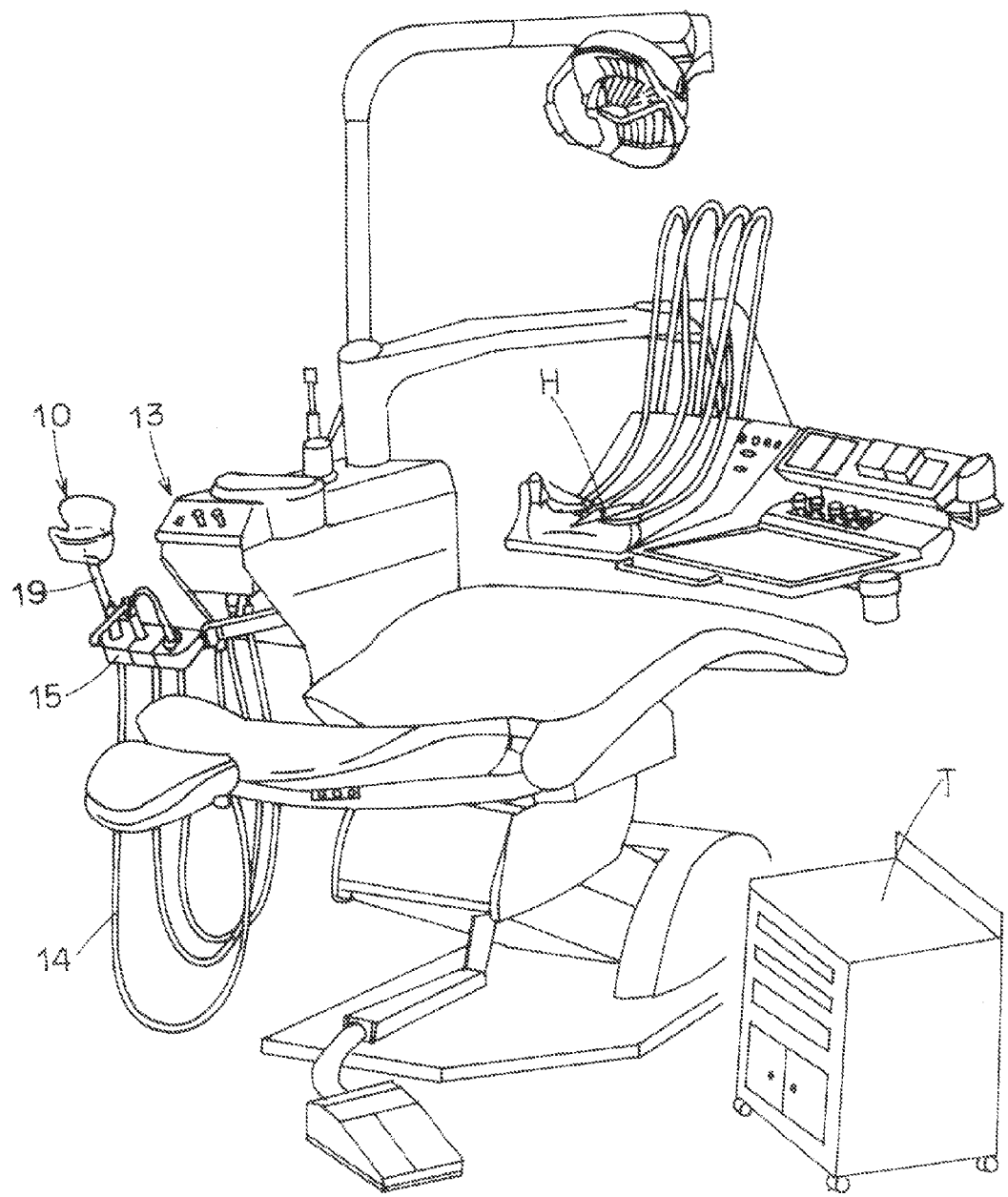
FIG. 2 is a general perspective view of a dental unit engaged with the hooded simple suction tray for dental extraoral operations according to Embodiment 1 of the present invention.
Figure 3:
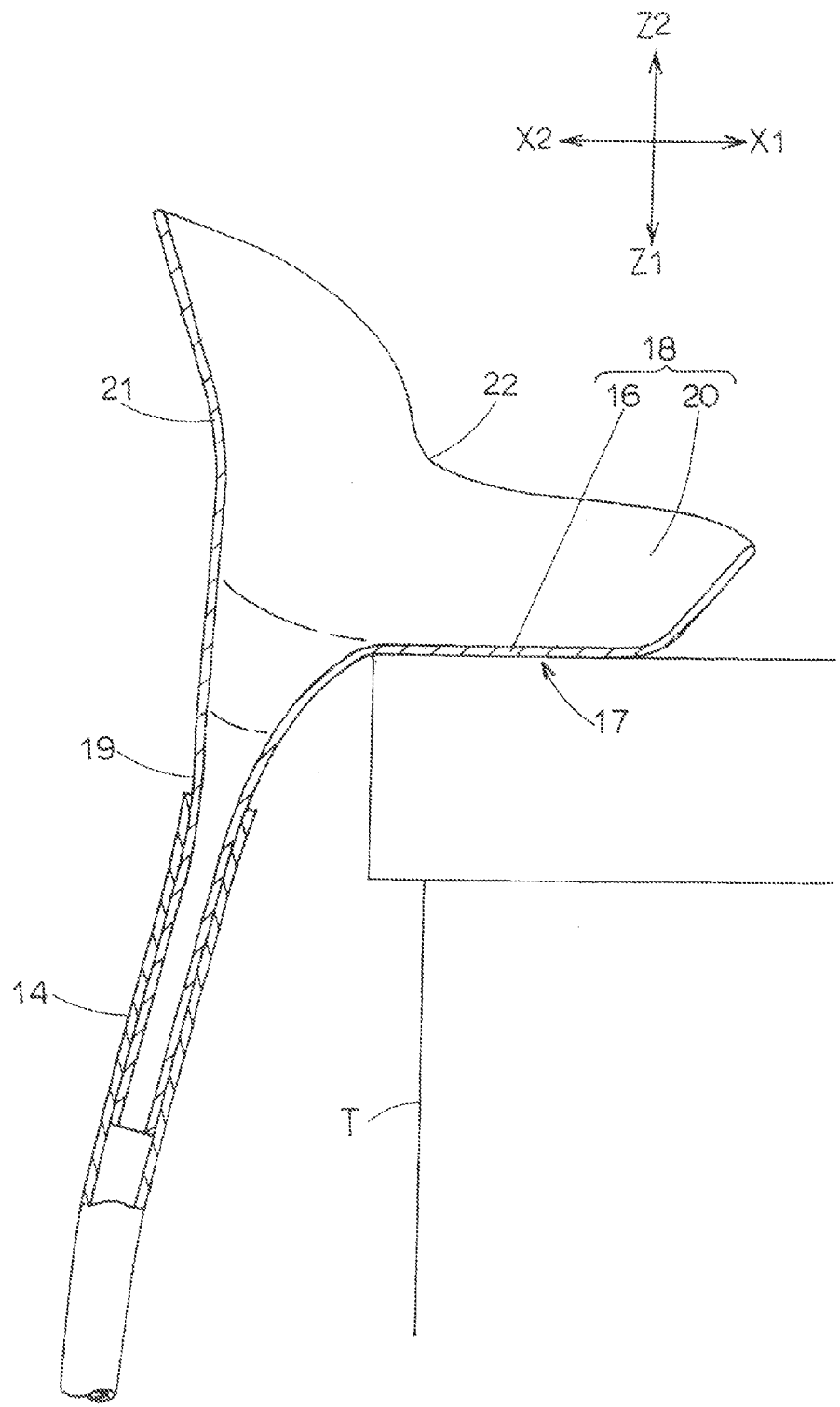
FIG. 3 is a vertical cross-sectional view of the hooded simple suction tray for dental extraoral operations according to Embodiment 1 of the present invention hooked to and mounted on a working table for denture adjustment.

As depicted in FIGS. 1 to 3, the hooded simple suction tray 10 connected to the suction hose 14 of the dental suction apparatus 13 via the communication pipe 19 is attached to the working table T by hooking the base hooking and mounting portion 17 with the flat lower surface on an end of an upper plate of the table. Thus, during the use of the hooded simple suction tray 10, the orientation of the tray is stabilized.

Figure 5:
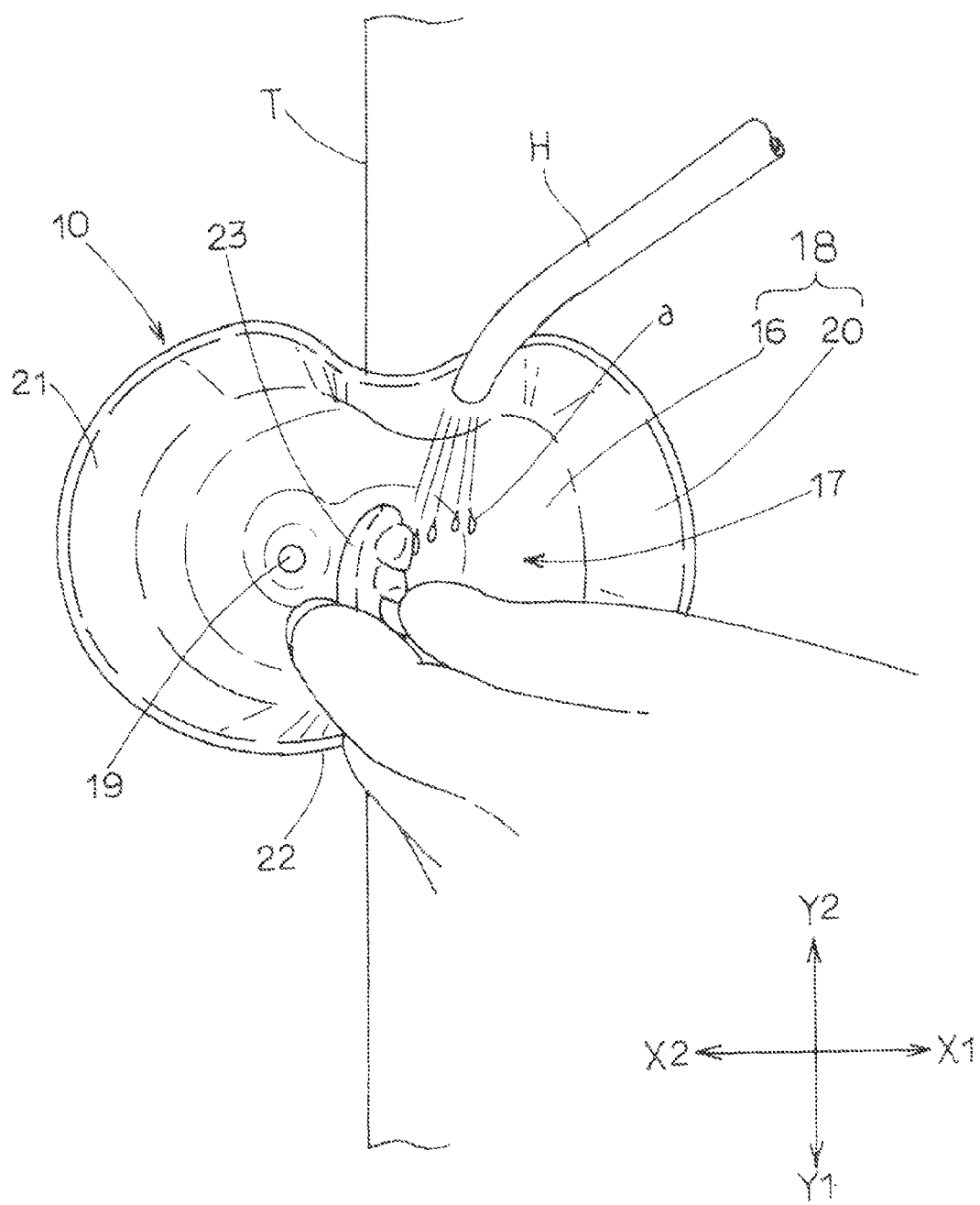
FIG. 5 is plan view depicting a denture washing operation state using the hooded simple suction tray for dental extraoral operations according to Embodiment 1 of the present invention.

Subsequently, adjustment operations for a denture 23 such as cutting, grinding, and polishing are performed in the internal space of the tray main body 18 using a hand piece H (FIG. 4). Furthermore, the denture 23 is washed using washing water (FIG. 5).

While prevented by the fly prevention hood 21 from flowing out from the tray, flying substances (a) such as denture chips and powder and used washing water which result from the above-described extraoral operations are sucked into the dental suction apparatus 13 through the suction hose 14 and the communication pipe 19 under a negative pressure generated by the dental suction apparatus 13. Substances having failed to be sucked, for example large denture chips, are collected on the bottom plate 16 of the hooded simple suction tray 10.

Thus, compared to the conventional suction apparatus, the suction apparatus according to the present invention can be reduced in overall size and costs. Moreover, the suction apparatus according to the present invention can suck not only solids such as denture chips and powder resulting from extraoral operations and foul smell and gas resulting from the operations but also liquids such as washing water used for the operations, without using a medical tray for the conventional method or the like and without causing the solids, smell, gas, and liquids to be released outward.

Furthermore, during extraoral operations, the operator can perform the operation with the operator's fingers placed on the finger placing portions 22 at the junctions of the upper edge of the peripheral side plate 20 which are connected to the opposite ends of the fly prevention hood 21 in a width direction thereof. Thus, the operator's hands are unlikely to be fatigued even if the extraoral operation takes much time.

Now, a hooded simple suction tray for dental extraoral operations according to Embodiment 2 of the present invention will be described with reference to FIG. 6.

Figure 6:
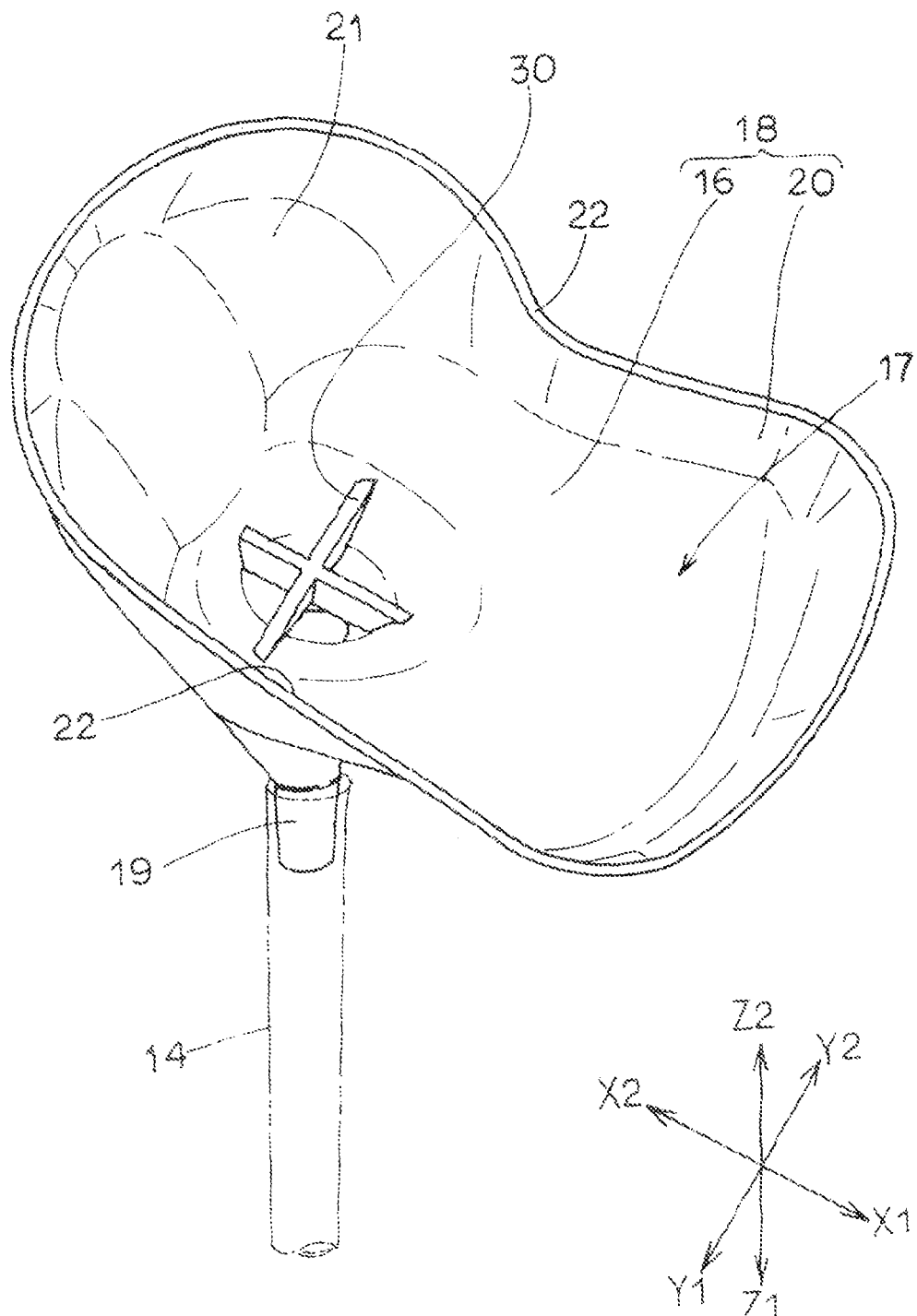
FIG. 6 is perspective view depicting another hooded simple suction tray for dental extraoral operations according to Embodiment 1 of the present invention.

As depicted in FIG. 6, a simple suction tray 10A according to Embodiment 2 of the present invention is characterized in that a foreign substance entry prevention frame 30 appearing like a cross in plan view is attached to an opening at an upper end of a communication pipe 19, for example, to prevent large denture chips resulting from denture adjustment from entering and blocking the communication pipe 19. The foreign substance entry prevention frame 30 may be removably fitted into the communication pipe 19. Alternatively, instead of the cross-like foreign substance entry prevention frame 30, a foreign substance entry prevention net (tea strainer-like net) may be removably or fixedly installed at the upper opening of the communication pipe 19 so as to allow finer denture chips to be also captured.

The remaining part of the configuration and the other effects are the same as the corresponding part of the configuration and the corresponding effects of Embodiment 1 and will thus not be described below.

INDUSTRIAL APPLICABILITY

The present invention is useful as a technique for allowing extraoral operations such as denture adjustment to be hygienically and efficiently performed.

REFERENCE SIGNS LIST 10, 10A Hooded simple suction tray for dental extraoral operations
13 Dental suction apparatus
14 Suction hose
16 Bottom plate
17 Base hooking and mounting portion
18 Tray main body
19 Communication pipe
20 Peripheral side plate
21 Fly prevention hood
22 Finger placing portion
T Working table
a Flying substance

What is claimed is:

1. A hooded simple suction tray for dental extraoral operations which is installed in a suction hose for a dental suction apparatus incorporated in a dental unit and which is removably held by a nozzle holder of the dental unit, wherein the hooded simple suction tray includes: a tray main body having an internal space in which an extraoral operation is performed; a communication pipe that allows the internal space of the tray main body and the suction hose to communicate with each other; and a fly prevention hood that prevents a flying substance resulting from the extraoral operation from flying around, the tray main body, the communication pipe, and the fly prevention hood being integrally formed of a synthetic resin, and wherein the tray main body includes a substantially rectangular bottom plate that is long in an X1-X2 direction and short in a Y1-Y2 direction orthogonal to the X1-X2 direction in a plan view and a peripheral side plate that stands from a peripheral portion of the bottom plate and inclining gradually outward in an upward direction, the bottom plate includes a base hooking and mounting portion formed on the bottom plate and having a partly flat lower surface, the communication pipe extends downward from the bottom plate and is attached to an X2-side end portion of the bottom plate in the X1-X2 direction, with this X2-side end portion being corresponding to an intermediate portion of the bottom plate in the Y1-Y2 direction, the communication pipe is a funnel-shaped pipe that has a diameter gradually increasing upward, the fly prevention hood includes a petal-shaped plate which is erected at a communication pipe-side upper end portion of the peripheral side plate and which gradually decreases outward in length in the Y1-Y2 direction, gently recessed finger placing portions are arranged in an area of the base hooking and mounting portion, on junctions of an upper edge of the peripheral side plate which are connected to opposite ends of the fly prevention hood in the Y1-Y2 direction, the bottom plate has a maximum length of 6 cm to 8 cm in the X1-X2 direction and a maximum length of 2 cm to 6 cm in the Y1-Y2 direction, and the base hooking and mounting portion is hooked to and mounted at an end portion of an upper surface of a work table to allow the extraoral operation to be performed.

* * * * *